United States Patent [19]
McMichael et al.

[11] Patent Number: 5,798,102
[45] Date of Patent: Aug. 25, 1998

[54] TREATMENT OF CARDIOMYOPATHY

[75] Inventors: John McMichael, Delanson, N.Y.; Harry C. Gurney, Conifer, Colo.

[73] Assignee: Milkhaus Laboratory, Inc., Delanson, N.Y.

[21] Appl. No.: 810,725

[22] Filed: Mar. 4, 1997

[51] Int. Cl.⁶ .......................... A61K 38/16; A61K 38/48; A61K 38/27

[52] U.S. Cl. .......................... 424/198.1; 424/94.1; 514/8; 514/21

[58] Field of Search .............................. 424/94.1, 198.1; 514/8, 21

[56] References Cited

U.S. PATENT DOCUMENTS

| | | |
|---|---|---|
| 4,294,818 | 10/1981 | McMichael et al. |
| 4,521,405 | 6/1985 | McMichael et al. |
| 4,666,829 | 5/1987 | Glenner et al. |
| 4,704,273 | 11/1987 | McMichael |
| 4,705,685 | 11/1987 | McMichael |
| 4,816,416 | 3/1989 | Averback |
| 4,880,626 | 11/1989 | McMichael |
| 4,912,206 | 3/1990 | Goldgaber et al. |
| 5,187,153 | 2/1993 | Cordell et al. |
| 5,223,482 | 6/1993 | Schilling, Jr. et al. |

FOREIGN PATENT DOCUMENTS

| | | |
|---|---|---|
| WO 91/16819 | 11/1991 | WIPO |
| WO 95/31996 | 11/1995 | WIPO |

OTHER PUBLICATIONS

Gupta et al Toxicon(1980) vol. 18(3) 389–91.

Razin et al., *Proc. Natl. Acad. Sci. (USA)*, 91:7722–7726 (1994).

Fazio et al., "A preliminary study of growth hormone in the treatment of dilated cardiomyopathy," *The New England Journal of Medicine*, 334:No. 13, 811–814 (1996).

Fazio et al., "Growth hormone in the treatment of dilated cardiomyopathy," *The New England Journal of Medicine*, 335:No. 9, 672–674 (1996).

Allen, "Is RA27/3 Rubella Immunization a Cause of Chronic Fatigue?", *Medical Hypotheses*, 27:217–220 (1988).

Anderton et al., "Monoclonal antibodies show that neurofibrillary tangles and neurofilaments share antigenic determinants," *Nature*, 298:84–86 (Jul. 1, 1982).

Bahmanyar et al., "Amyloid Plaques in Spongiform Encephalopathy of Mule Deer," *J. Comp. Path.*, 95:1–5 (1985).

Bahmanyar et al., "Characterization of Antineurofilament Autoantibodies in Creutzfeldt–Jakob Disease, " *J. Neuropathol. Exp. Neurol.*, 43(4):369–375 (Jul. 1984).

Bahmanyar et al., "Serum Antibodies to Neurofilament Antigens in Patients with Neurological and Other Disease and in Healthy Controls," *J. Neuroimmunol.*, 5:191–196 (1993).

Baudry et al., "Low Levels of Calpain Activity in Chiropera Brain: Implications for Mechanisms of Aging," *Neurobiol. Aging*, 7:255–258 (1986).

Bruce, "Amyloid Plaques in Experimental Scrapie: Factors Influencing the Occurence of Cerebral Amyloid in Inbred Mice," *J. Nueorpathol. Exp. Neurol.*, 37:595 (1978).

Bruist et al., "Synthesis of a Site–Specific DNA–Binding Peptide," *Science*, 235:777–780 (Feb. 13, 1987).

Castano et al., "In Vitro Formulation of Amyloid Fibrils from Two Synthetic Peptides of Different Lengths Homologous to Alzheimer's Disease β–Protein," *Biochem. Biophys. Res. Com.*, 141(2):782–789 (Dec. 15, 1986).

Cohen and Calkins, "Electron Microscopic Observations on a Fibrous Component in Amyloid of Diverse Origins," *Nature*, 183:1202–1203 (Apr. 25, 1959).

Cohen and Calkins, "The Isolation of Amyloid Fibrils and a Study of the Effect of Collagenase and Hyaluronidase," *J. Cell. Biol.*, 183:481–486 (1964).

Cohen et al., "Analysis of Histology and Staining Reactions of Casein–Induced Amyloidooiss in the Rabbit," *Am. J. Pathol.*, 35(5):971–989 (Sep.–Oct. 1959).

Dahl and Bignami, "Immunochemical Cross–Reactivity of Normal Neurofibrils and Aluminum–Induced Neurofibrillary Tangles," *Exp. Neurol.*, 58:74–80 (1978).

Elizan et al., "Antineurofilament Antibodies in Postencephalitic and Idiopathic Parkinson's Disease," *J. Neurol. Sci.*, 59:341–347 (1983).

Gajdusek, "Hypothesis: Interface with Axonal Transport of Neurofilament as a Common Pathogenic Mechanism in Certain Diseases of the Central Nervous System," *New Eng. J. Med.*, 312(11):714–719 (Mar. 14, 1985).

Ghiso et al., "Alzheumer's Disease Amyloid Precursor Protein is Present in Senile Plaques and Cerebrospinal Fluid: Immunohistochemical and Biochemical Characterization," *Biochem. Biophys. Res. Com.*, 163(1):430–437 (Aug. 30, 1989).

Glenner, "Alzheimer's Disease The Commonest Form of Amyloids," *Arch. Pathol. Lab. Med.*, 107:281–282 (Jun. 1983).

Glenner and Wong, "Alzheimer's Disease and Down's Syndrome: Sharing of a Unique Cerebrovascular Amyloid Fibril Protein," *Biochem. Biophys. Res. Com.*, 122(3):1131–1135 (1984).

Goldman et al., "Cytoplasmic Fibers in Mammalian Cells: Cytoskeletal and Contractile Elements," *Ann. Rev. Physiol.*, 41:703–722 (1979).

Griffin et al., "slow Axonal Transport of Neurofilament Proteins: Impairment by β, β'–Iminodipropionitrile Administration," *Science*, 202:633–635 (Nov. 1978).

Hoffman and Lasek, "The Slow Component of Axonal Transport," *J. Cell. Biol.*, 66:351–366 (1975).

(List continued on next page.)

*Primary Examiner*—Lila Feisee
*Assistant Examiner*—Geetha P. Bansal
*Attorney, Agent, or Firm*—Marshall, O'Toole, Gerstein, Murray & Borun

[57] ABSTRACT

The invention presents methods for the treatment of symptoms associated with cardiomyopathy comprising treatment with an effective amount of a composition comprising beta-amyloid, streptolysin O, and growth hormone.

12 Claims, No Drawings

OTHER PUBLICATIONS

Howard and Pilkington, "Antibodies to fibronectin bind plaques and other structures in Alzheimer's disease and control brain," *Neuroscience Letters*, 118:71–76 (1990).

Iqbal et al., "Chemical Relationship of the Paired Helical Filaments of Alzheimer's Dementia to Normal Human Neurofilaments and Neurotubules," *Brain Res.*, 142:321–332 (1978).

Itagaki, et al., "Presence of T–Cytotoxic Supressor and Leukocyte Common Antigen Positive Cells in Alzheimer's Disease Brain Tissue," *Neuroscience Letters*, 91:259–264 (1988).

Joachim and Selkoe, "Amyloid Protein in Alzheimer's Disease," *J. Gerontology*, 44:(4):B77–84 (1989).

Jones et al., "Evidence for Active Epstein–Barr Virus Infection in Patients with Persistent, Unexplained Illnesses: Elevated Anti–Early Antigen Antibodies," *Annals of Internal Medicine*, 102:1–6 (Jan. 1985).

Kang et al., "The precursor of Alzheimer's disease amyloid A4 resembles a cell–surface receptor," *Nature*, 325:733–736 (Feb. 19, 1987).

Kilbourne, "Inactivated Influenza Virus Vaccines" in *Vaccines*, pp. 420–434, Plotkin et al., Eds., W.B. Saunders Company, Philadelphia (1988).

Knight, "Dopamine–Receptor–Stimulating Autoantibodies: A Possible Cause of Schizophrenia," *Lancet*, 82:1073–1076 (Nov. 13, 1982).

Komaroff, "The 'Chronic Mononucleosis' Syndromes," *Hospital Practice*, 71–75 (May 30, 1987).

Lasak, "The Dynamic Ordering of Neuronal Cytoskeletons," *Neurosciences. Res. Prog. Bull.*, 19(1):7–32 (1981).

Lieberman, "The Role of the Rubella Virus In The Chronic Fatigue Syndrome," *Clinical Ecology*, 7(3):51–54 (1990).

Marx, "A New Link in the Brain's Defenses," *Science*, 256:1278–1280 (May 29, 1992).

Marx, "Testing of Autoimmune Therapy Begins," *Science*, 252:27–28 (Apr. 5, 1991).

Masters et al., "Amyloid plaque core protein in Alzheimer disease and Down syndrome," *Proc. Natl. Acad. Sci. USA*, 82:4245–4249 (Jun. 1985).

Melnick et al., "Possible Role of Cytomegalovirus in Atherogenesis," *JAMA*, 263(16):2204–207 (Apr. 25, 1990).

Miller, "A Double–Blind Study of Food Extract Injection Therapy: A Preliminary Report," *Annals of Allergy*, 38:185–191 (Mar. 1977).

Miller, "Influenza: Rapid Relief Without Drugs," *Clinical Medicine*, 81:16–19 (Sep. 1974).

Moos and Solomon, "Psychologic Comparisons Between Women with Rheumatoid Arthritis and Their Nonarthritic Sisters," *Psychosom. Med.*, 27(2):135–149 (1965).

Newcombe and Cohen, "Solubility Characteristics of Isolated Amyloid Fibrils," *Biochem. et Biophys. Acta*, 104:480–486 (1965).

Rabins and Folstein, "The Dementia Patient: Evaluation and Care," *Geriatrics*, 38(8):99–117 (Aug. 1983).

Reines, "Early Clinical Trials in Alzheimer's Disease: Selection and Evaluation of Drug Candidates," *Progress in Clin. Biol. Res.*, 1283–1290 (1989).

Samet, Peptides Offer Promise for Treating Alzheimer's and other Neurodiseases, *Genetic Engineering News*, p. 24 (Jul./Aug. 1991).

Selkoe et al., "Isolation of Low–Molecular–Weight Proteins from Amyloid Plaque Fibers in Alzheimer's Disease," *J. Neurochem.*, 46:1820–1834 (1986).

Shacks et al., "Increased Serum IgG4 Levels in Acute Epstein–Barr Viral Mononucleosis," *Annals of Allergy*, 54:284–288 (Apr. 1985).

Shelanski and Leim, "Neurofilaments," *J. Neurochem.*, 33:5–13 (1979).

Snow and Wight, "Proteoglycans in the Pathogenesis of Alzheimer's Disease and Other Amyloidoses," *Neurobio. Aging.*, 10:481–497 (1989).

Solomon "Psychoneuroimmunology: Interactions Between Central Nervous System and Immune System," *J. Neurosci. Res.*, 18:1–9 (1987).

Solomon and Moos, "Emotions, Immunity, and Disease," *Arch. Gen. Psychiatry*, 11:657–674 (Dec. 1964).

Strauss et al., "Persisting Illness and Fatigue in Adults with Evidence of Epstein–Barr Virus Infection," *Annals of Internal Medicine*, 102:7–16 (1985).

Tanzi et al., "Amyloid β Protein Gene: cDNA, mRNA Distribution, and Genetic Linkage Near the Alzheimer Locus," *Science*, 235:880–884 (Feb. 20, '1987).

Tingle et al., "Prospective Immunological Assessment of Arthritis Induced by Rubella Vaccine, " *Infect. Immun.*, 40(1):22–28 (Apr. 1983).

Turnell et al., "Secondary Structure Prediction of Human $SAA_1$Presumptive Identification of Calcium and Lipid Binding Sites," *Mol. Biol. Med.*, 3:387–407 (1986).

Turnell et al., "X–Ray Scattering and Diffraction by Wet Gels of AA Amyloid Fibrils," *Mol. Biol. Med.*, 3:409–424 (1986).

Wirak et al., "Deposits of Amyloid β Protein in the Central Nervous System of Transgenic Mice," *Science*, 253:323–325 (Jul. 19, 1991).

Wong et al., "Neutric plaques and cerebrovascular amyloid in Alzheimer disease are antigenically related," *Proc. Natl. Acad. Sci. USA*, 82:8729–8732 (Dec. 1985).

Yanker et al., "Neurotrophic and Neurotoxic Effects of Amyloid β Protein: Reversal by Tachykinin Neuropeptides," *Science*, 250:279–282 (Oct. 12, 1990).

Zurawaki et al., "Activation of Mouse T–Helper Cell Induces Abundant Preproenkephalin mRNA Synthesis," *Science*, 232:772–775 (May 9, 1986).

Loh et al., "Growth hormone for heart failure—Cause for caution optimism," *The New England Journal of Medicine*, 334:No. 13, 856–857 (1996).

TREATMENT OF CARDIOMYOPATHY

FIELD OF INVENTION

This invention relates generally to methods and materials for the treatment and amelioration of the symptoms associated with cardiomyopathy.

BACKGROUND OF THE INVENTION

Cardiomyopathy is a disease of the heart muscle. This form of heart disease is often distinctive, both in general symptoms and in patterns of blood flow, to allow a diagnosis to be made. Increasing recognition of this disease, along with improved diagnostic techniques, has shown that cardiomyopathy is a major cause of morbidity and mortality. In some areas of the world it may account for as many as 30 percent of all deaths due to heart disease.

Cardiomyopathy can result from a variety of structural or functional abnormalities of the ventricular myocardium. A large number of cardiomyopathies are apparently not related to an infectious process and are not well understood. Some are congenital and may cause enlargement of the heart. Metabolic diseases associated with endocrine disorders may also cause cardiomyopathies. Infections, such as acute rheumatic fever and several viral infections, may cause a number of types of myocarditis. Myocarditis may also occur as a manifestation of a generalized hypersensitivity reaction, allergic or immunologic. The heart may also be affected by any of a considerable number of collagen diseases. Collagen is the principal connective tissue protein, and collagen diseases are diseases of the connective tissues. They include diseases primarily of the joints, skin, and systemic disease.

There are three clinical classifications of cardiomyopathy; hypertrophic, restrictive, and dilated congestive. Dilated congestive cardiomyopathy is a disorder of myocardial function where ventricular dilation occurs, often following virus infection. Restrictive cardiomyopathy occurs as a consequence of the ventricular walls becoming rigid so that the chambers are unable to fill adequately. This is usually idiopathic. Hypertrophic cardiomyopathy is characterized by ventricular hypertrophy and may be congenital or acquired. The prognosis for all three types of disease is guarded at best and often poor. Treatment of cardiomyopathy involves restricted activity, stress avoidance, treatment with beta-blockers, prophylactic antibiotic therapy, use of anti-coagulants, calcium channel blockers, surgery, and cardiac transplantation.

Of interest to the present application are the disclosure of co-owned published PCT international applications PCT/US91/01898 published Nov. 14, 1991, PCT/US95/06689 published Nov. 30, 1995 and co-owned and copending U.S. patent application Ser. No. 08/689,528 filed Aug. 8, 1996 the disclosures of which are hereby incorporated by reference. These references relate in part to methods for alleviating symptoms associated with amyloid plaque formation and/or formation of arterial plaques comprising the step of administering to a patient an effective amount of amyloid protein.

Recent literature reports have focused on the use of somatotropin, a growth hormone, for the treatment of cardiomyopathy. See: "A Preliminary Study of Growth Hormone in the Treatment of Dilated Cardiomyopathy", *N.E. J. of Medicine*, 334(13), pp. 811–814 (1996). However, cautionary responses to such reports speak to the possibility, or even likelihood, of inducing cancer, arrhythmias, and other problems with growth hormone therapy using the concentrations now being evaluated by those authors. Accordingly, there remains a desire in the art for effective cardiomyopathy therapies that allow reduction in the amount of growth hormone administered and do not suffer from the limitations of the prior methods.

SUMMARY OF THE INVENTION

The present invention relates to the discovery that treatment of cardiomyopathy with a combination of compounds is effective in improving heart function. The therapeutic composition described herein is comprised of three compounds, each with a specific function relative to the amelioration of symptoms associated with cardiomyopathy. They are: beta-amyloid protein, streptolysin O, and growth hormone. It has been found that the administration of these compounds in combination is surprisingly effective in treating the symptoms associated with cardiomyopathy and allows a reduction in the amount of growth hormone required for a useful therapeutic effect.

Beta-amyloid acts to reduce vascular plaquing that may be associated with the disease. Streptolysin O reduces or eliminates cardiac scarring associated with the heart disease. Streptolysin O is one of a group of filterable hemolysins derived from Group A beta-hemolytic streptococci. Specifically, streptolysin O is a 60 kD peptide which is hemolytic in its reduced state but is inactivated upon oxidation. Streptolysin O is used in the art generally as an analytical reagent for permeabilizing cells. See, e.g., Razin et al., *Proc. Nat'l. Acad. Sci. (USA)*, 91:7722–7726 (1994). Co-owned U.S. Pat. No. 5,576,289, the disclosure of which is incorporated by reference, discloses the use of streptolysin O in methods for treating disease states characterized by motor deficit disorders. No disclosure is made in that patent of utility of streptolysin O in treating cardiomyopathy.

Growth hormone stimulates healing of the compromised heart. Growth hormone functions to regulate somatic growth and also maintains muscle mass and strength. It can also act as a counterregulatory hormone opposing the action of insulin on carbohydrate and lipid metabolism.

It has been discovered that by administration of a combination of the above compounds symptoms associated with cardiomyopathy are reduced or stabilized. The present invention provides methods for treating cardiomyopathy by administration of an effective amount of a composition comprising beta-amyloid, streptolysin O, and growth hormone. Methods of the invention result in amelioration of the symptoms associated with cardiomyopathy such as angina, fatigue, loss of strength, respiratory insufficiency, edema, interrupted sleep, recurrent respiratory infection, and the like. Noticeable improvement and/or stabilization of the disease symptoms were obtained after treatment. Improved Ejection Fraction (EF), blood pressure, and echo cardiogram readings were also noted in some cases.

The invention comprises the step of administering an effective amount of beta-amyloid, streptolysin O, and growth hormone in combination, to a patient suffering from cardiomyopathy. The precise dose will vary among patients and may readily be determined by those skilled in the art. Useful dosages generally range from about $1\times10^{-11}$ mg to 10 mg of beta-amyloid, about 0.0005 units to 50 units streptolysin O, and about $1\times10^{-16}$ I.U. to 100 I.U. growth hormone, with preferred dosages of from about $10^{-7}$ mg to 1.0 mg, 0.1 units to 10 units, and $10^4$ I.U. to 10 I.U., of each compound respectively. It is particularly preferred that dosages of about 0.1 I.U. or less of growth hormone be used to minimize potential negative effects of growth hormone therapy. Most preferred is the use of growth hormone at dosages of 0.01 I.U. or less. The compositions of the invention may be administered by a variety of routes of administration including intravenous, intramuscular, subcutaneous, intrathecal, and oral, with sublingual administration being preferred. It is also anticipated that alternative routes of administration may be by inhalation and topical application.

The preferred dosage for sublingual application is 1–10 drops (0.05 ml/drop) per day according to the above formula. Subcutaneous injections are administered 1–3 times a day. Additional aspects and advantages of the invention will become apparent upon consideration of the following detailed description thereof.

DETAILED DESCRIPTION OF THE INVENTION

It has been discovered that treatment of a patient suffering from cardiomyopathy with a composition comprising beta-amyloid, streptolysin O, and growth hormone can reduce or stabilize the disease symptoms. Administration of the composition of the invention has been shown to be effective in clinical improvement in angina, energy, and strength. It has also been shown to have a stabilizing effect on echocardiogram testing indicating improved cardial function and efficiency.

A number of animal and human clinical trials have been conducted and the results are presented herein in the form of several examples. In each human test case, clinical histories of the patients were known or taken prior to treatment according to the invention. In the reported examples, reduction or stabilization of the adverse symptoms of cardiomyopathy were noted. In some cases, improved EF ratings were observed after treatment according to the invention, along with increased energy and strength. In treatment of dogs of various breeds, ages, and sizes, disease symptoms either remained stable or improved without adverse effects. In 70% of the cases, improved performance, endurance, and vitality were observed in dogs.

Compositions according to the invention comprise effective combinations of from about $1 \times 10^{-10}$ to about $1 \times 10$ mg beta-amyloid, from about 0.0005 units to about 50 units streptolysin O, and from about $1 \times 10^{-6}$ International Units (I.U.) to about 100 I.U. growth hormone. According to a preferred embodiment, a composition is provided which comprises about $4 \times 10^{-9}$ mg beta-amyloid, about 2 units streptolysin O, and less than 4 I.U. of human growth hormone with less than 0.1 I.U. being preferred and about 0.01 I.U. growth hormone being particularly preferred. Growth hormone used in this invention can be of a human, porcine, bovine, or other source, and can be produced by recombinant methods.

Proper dosing of the composition of the present invention may easily be determined by the skilled artisan using standard procedures and upon evaluation of the severity of a patient's symptoms. The compositions of the invention may be formulated in an appropriate pharmaceutical vehicle, including water, saline, dextrose, and albumin.

In the present invention, human patients in the foregoing examples were treated using relatively low doses of the compositions. Drops were administered daily of a composition comprising $4 \times 10^{-9}$ mg beta-amyloid, 2 units streptolysin O, and 0.01 I.U. growth hormone. The preferred route of administration was sublingually and patients were generally instructed to self-administer from one to about 6 drops daily.

Provided below are case histories of patients being treated according to the invention which provide evidence of the effectiveness of the treatment methods described herein.

The following Examples are intended to illustrate practice of the preferred embodiments of the invention. Numerous additional embodiments and improvements are apparent upon consideration of the following Examples.

EXAMPLE 1

Forty dogs of varied ages, breeds, and exhibiting symptoms of cardiomyopathy were treated with a 0.2 cc subcutaneous injection of the composition of the invention comprising $4 \times 10^{-9}$ mg beta-amyloid, 2 units streptolysin O and 0.01 I.U. growth hormone. Prior to treatment, the dogs were lethargic, depressed, and easily exhausted. After treatment of several weeks to several months, the dogs exhibited noticeable improved performance and energy. Significant improved activity performance and vitality was observed in 70% of the dogs.

EXAMPLE 2

A 74-year-old white male with a history of cardiomyopathy was treated according to the methods and compositions of the invention. The patient received 4 drops a day of a composition comprising $4 \times 10^{-9}$ mg beta-amyloid, 2 units streptolysin O, and 0.01 I.U. growth hormone. His initial ejection fraction (EF) by echocardiogram was 35%, while three months later it had improved to 50%. A repeat echocardiogram was not readable at the six-month evaluation, however, a MUGA (multiple gated acquisition) scan revealed a normal EF of 53%. This reading was significantly better than the baseline EF of 35%, even with the variation in echocardiogram versus MUGA EF determinations. After approximately 6 months of treatment, the patient's blood pressure was 140/70 with a heart rate of 68. One month later, his blood pressure was 122/82 with only one episode of chest pain. A significant improvement in left ventricular function was noted. The patient has reported increased energy and strength and reported no angina symptoms for one month.

EXAMPLE 3

A 73-year-old white male with a history of multiple cardiomyopathic symptoms was treated according to the procedure set out in Example 2. His initial EF by echocardiogram was 25%, while three months after treatment, his EF was 20%. At the six-month evaluation, he had 2+ edema (nonpitting) and a repeat echocardiogram revealed an EF of 25–30% compared to a baseline of 25%. The patient's blood pressure was 142/70. The patient reported dramatic clinical improvement in angina, energy, and strength. After another month of treatment, his echocardiogram EF remained unchanged, but he continued to have no angina, good energy levels, and strength. He also reported that when he stopped using the composition after 2–3 days, he had pain across his anterior chest and became more fatigued and complained of less strength.

EXAMPLE 4

A 70-year-old white female with a history of multiple medical problems, including cardiomyopathy, was treated according to the procedure set out in Example 2. This patient had multiple admissions to the hospital with recurrent angina and congestive heart failure. Her EF remained severely depressed at 10–15% after seven months treatment. She had severe coronary artery disease and prognosis was poor. The patient had periods of improvement clinically, but this was earlier in treatment according to the invention. Her initial EF by echocardiogram was 15–20%, while three months later it was 10–15%. It has remained stable for an additional three months. She recently suffered another episode of angina and her EF remains at 10%. It is believed advanced coronary disease prevented a more positive response to the compositions of the invention.

EXAMPLE 5

An 86-year-old white male with a history of a dilated cardiomyopathy and an EF of 25% by a chemical stress sestamibi prior to treatment according to the invention. He also had moderately severe chronic obstructive pulmonary disease (COPD). His main symptoms include dyspnea and palpitations, especially during exertion, extreme fatigue, lethargy, and shortness of breath. After one month of treatment with 1 drop of a composition, according to Example 2, four times daily, his blood pressure was 142/80 and his lungs were clear but decreased. His pulse was 72.

After two months of treatment, he was slightly improved and continued to have less severe dyspnea and less lethargy. He continued to be fatigued, but needed less sleep. Palpitations were present, but less frequent. His energy level was similar, although he was more active. There appeared to be slight clinical improvement overall after two months of treatment according to the therapy.

EXAMPLE 6

A 69-year-old white male with a history of ischemic cardiomyopathy, chronic atrial fib/flutter, COPD, diabetes mellitus type 2, congestive heart failure, and hyperlipidemia was treated with 1 drop four times daily according to the procedure in Example 2. An initial echocardiogram revealed an EF of 10–20%. Prior to treatment, this patient had been a virtual invalid and practically confined to a chair. He had tachycardia intermittently, extreme fatigue, and dyspnea with minimal exertion. He also had extreme shortness of breath. On the first day of treatment, his blood pressure was 102/70. His lung sounds were decreased and the heart rhythm was atrial fibrillation.

A month after treatment began, he was walking without shortness of breath and his energy improved. His palpitations, which were occurring daily, had occurred only once in two weeks. He had no chest pain. He continued to improve and had no palpitations or chest pain after two months of treatment. He developed dyspnea and palpitations, however, after physical exertion using a treadmill.

After an additional two weeks of treatment, the patient continued to significantly improve. He was no longer confined to a chair and is able to walk about throughout the day. His lungs were clear, but had a trace of edema. His blood pressure remained good.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A composition for treatment of cardiomyopathy in humans comprising an effective amount of beta-amyloid, streptolysin O, and growth hormone wherein said amount of growth hormone is from about $1 \times 10^{-6}$ International Units to about 0.1 International Units per dose.

2. The composition according to claim 1 wherein said amount of beta-amyloid is from about $1 \times 10^{-11}$ mg to about 10 mg, and streptolysin O is from about 0.005 to about 50 units per dose.

3. The composition according to claim 1 wherein said amount of beta-amyloid is about $4 \times 10^{-9}$ mg, streptolysin O is 2 Units per dose, and growth hormone is 0.01 International Units per dose.

4. The composition according to claim 1 wherein said amount of growth hormone is from about $1 \times 10^{-6}$ International Units to about 0.01 International Units per dose.

5. A method of ameliorating the symptoms of cardiomyopathy in humans comprising the step of administering from 1–10 drops per day to a patient diagnosed with cardiomyopathy an effective amount of beta-amyloid, streptolysin O, and growth hormone wherein said amount of growth hormone is from about $1 \times 10^{-6}$ International Units to about 0.1 International Units per dose.

6. The method according to claim 5, wherein said amount of beta-amyloid is from about $1 \times 10^{-11}$ mg to about 10 mg, and streptolysin O is from about 0.005 to about 50 units per dose.

7. The method according to claim 5 wherein said amount of beta-amyloid is about $4 \times 10^{-9}$ mg streptolysin O is 2 Units, and growth hormone is 0.01 International Units.

8. The method according to claim 5 wherein said growth hormone is from about $1 \times 10^{-6}$ International Units to about 0.01 Internal units per dose.

9. The method according to claim 5 wherein said composition is administered by a method selected for the group consisting of intramuscular, sublingual, intravenous, subctaneous, intrathecal, inhalation and topical.

10. The method according to claim 9 wherein said compound is administered sublingually.

11. The method of claim 9 wherein said compound is administered intravenously.

12. The composition of claim 1 in a pharmaceutically acceptable vehicle.

* * * * *

UNITED STATES PATENT AND TRADEMARK OFFICE
CERTIFICATE OF CORRECTION

PATENT NO. : 5,798,102  
DATED : August 25, 1998  
INVENTOR(S) : John McMichael and Harry C. Gurney Page 1 of 2

It is certified that error appears in the above-identified patent and that said Letters Patent is hereby corrected as shown below:

On the title page: Item [56]

Other Publications: At citation "Bahmanyar et al., delete "1993" and insert --1983--.

, Other Publications: At citation Cohen et al., delete "Amyloidooiss" and insert --Amyloidosis--.

Other Publications: At citation Ghiso et al., delete "Alzheumer's" and insert --Alzheimer's--.

, Other Publications: At citation Griffin et al., delete "slow" and insert --Slow--.

Pg. 2, Other Publications: At citation Kang et al., after: "...A4" insert --protein--.

UNITED STATES PATENT AND TRADEMARK OFFICE
CERTIFICATE OF CORRECTION

PATENT NO. : 5,798,102
DATED : August 25, 1998
INVENTOR(S) : John McMichael and Harry C. Gurney It is certified that error appears in the above-identified patent and that said Letters Patent is hereby corrected as shown below:

Col. 2, line 62: Delete "$10^4$", and insert - -$10^{-4}$- -.

Col. 6, line 38: After "Units ", insert - -per dose - - . (2nd occurrence)

Col. 6, line 46: Delete "subctaneous", and insert - -subcutaneous- -.

Signed and Sealed this

Twentieth Day of June, 2000

Q. TODD DICKINSON

*Attest:*

*Attesting Officer*     *Director of Patents and Trademarks*